US00PP30972P2

(12) United States Plant Patent
Chin et al.

(10) Patent No.: US PP30,972 P2
(45) Date of Patent: Oct. 22, 2019

(54) ***DRACAENA* PLANT NAMED 'HARVEST MOON'**

(50) Latin Name: *Dracaena deremensis*
Varietal Denomination: HARVEST MOON

(71) Applicant: Capri Farms, Inc., Homestead, FL (US)

(72) Inventors: Hugh Lincoln Chin, Miami, FL (US); Hector Levi Chin, Jr., Miami, FL (US)

(73) Assignee: CAPRI FARMS, INC., Homestead, FL (US)

( * ) Notice: Subject to any disclaimer, the term of this patent is extended or adjusted under 35 U.S.C. 154(b) by 0 days.

(21) Appl. No.: 15/932,917

(22) Filed: May 22, 2018

(51) Int. Cl.
*A01H 5/02* (2018.01)
*A01H 6/12* (2018.01)
*A01H 5/12* (2018.01)

(52) U.S. Cl.
USPC ..... Plt./383
CPC ..... *A01H 6/12* (2018.05); *A01H 5/02* (2013.01); *A01H 5/12* (2013.01)

(58) Field of Classification Search
USPC ..... Plt./383
CPC ..... A01H 5/12; A01H 5/02
See application file for complete search history.

*Primary Examiner* — Kent L Bell
(74) *Attorney, Agent, or Firm* — Foley & Lardner LLP

(57) ABSTRACT

A new and distinct *Dracaena* plant named 'HARVEST MOON' particularly characterized by its long, yellow-colored foliage with thin green variegated bands at the margins, some with pale cream-colored vertical stripes; slightly stiff, waxy leaf structure; upright growth habit with overall plant more wide than tall; general insect resistance with few mealybugs observed, and high tolerance for a wide range of light and water levels.

2 Drawing Sheets

Figure 1:
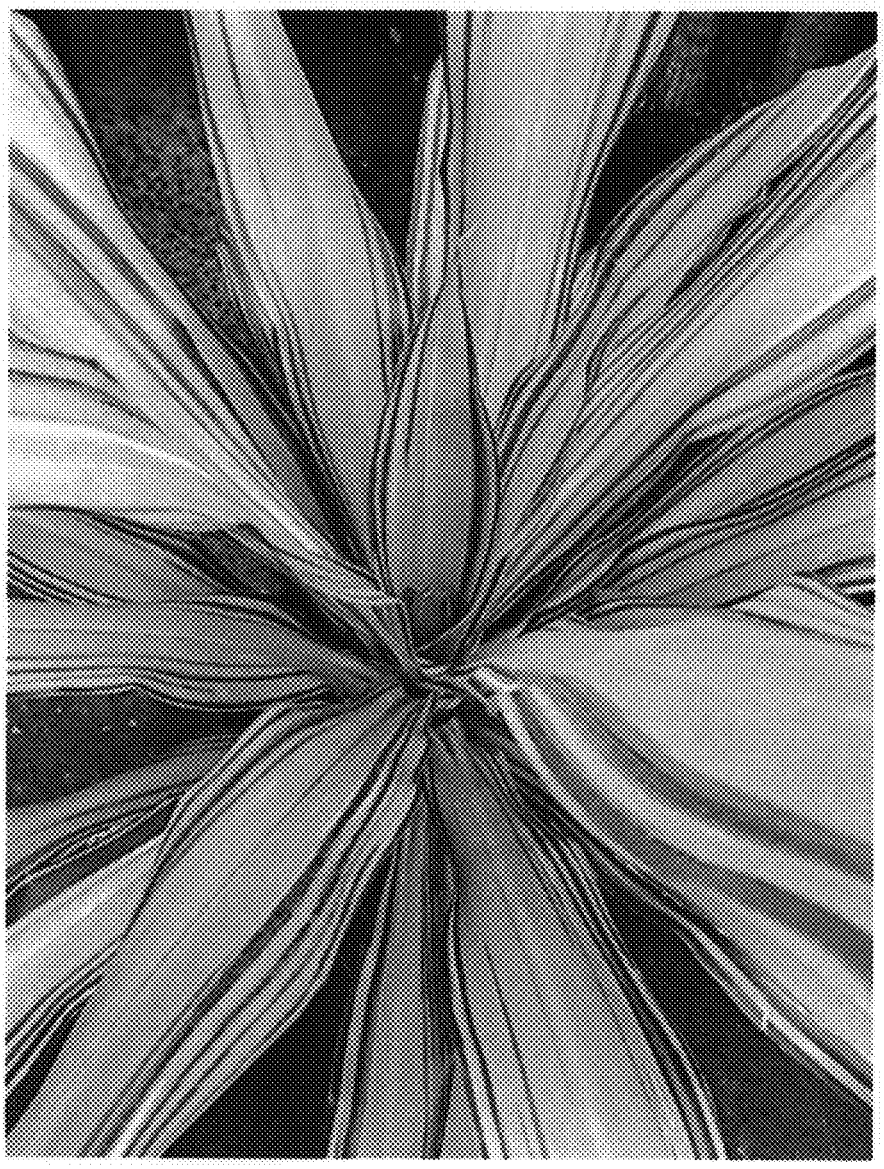

Latin name of the genus and species of the claimed plant: *Dracaena deremensis.*

Variety denomination: 'HARVEST MOON'.

BACKGROUND OF THE INVENTION

The present invention relates to a new and distinct cultivar of *Dracaena* plant, botanically known as *Dracaena deremensis*, of the family Asparagaceae, hereinafter referred to by the cultivar name 'HARVEST MOON'.

*Dracaena* is a monocotyledonous tropical foliage plant which can be produced as a single or multi-stemmed plant for interior use or outdoors in shade in zones 9 or 10 only.

The new *Dracaena* 'HARVEST MOON' originated as a naturally-occurring mutation of the *Dracaena* cultivar designated 'NOTCANE' (unpatented). The new *Dracaena* 'HARVEST MOON' was discovered and selected by the inventors in August 2014 as a single flowering plant mutation in a controlled environment in Homestead, Fla., USA.

Asexual reproduction of the new *Dracaena* cultivar by vegetative cuttings was first performed in June 2015 in Homestead, Fla., USA, and has demonstrated that the combination of characteristics as herein disclosed for the new cultivar are firmly fixed and retained through successive generations of asexual reproduction. The new cultivar reproduces true to type.

BRIEF SUMMARY OF THE INVENTION

The following traits have been repeatedly observed and are determined to be unique characteristics of 'HARVEST MOON', which in combination distinguish this *Dracaena* as a new and distinct cultivar:

1. Long, yellow-colored foliage with thin green variegated bands at the margins, some with pale cream-colored vertical stripes;
2. Slightly stiff, waxy leaf structure;
3. Upright growth habit, more wide than tall;
4. Mostly insect resistant, with few mealybugs observed; and
5. High tolerance for a wide range of light and water levels.

Plants of the new *Dracaena* 'HARVEST MOON' differ from plants of the parental cultivar, 'NOTCANE' (unpatented) in the characteristics described in Table 1.

TABLE 1

Comparison between 'HARVEST MOON' and 'NOTCANE'

| Characteristic | New Cultivar 'HARVEST MOON' | 'NOTCANE' (unpatented) |
|---|---|---|
| Leaf Color | Bright yellow with thin green stripes | Green with yellow center and broad green bands on edges |

Of the many commercial cultivars known to the present inventor, the most similar in comparison to the new *Dracaena* 'HARVEST MOON' is the *Dracaena* 'JANET CRAIG' (unpatented), in the characteristics described in Table 2:

TABLE 2

Comparison between 'HARVEST MOON' and 'JANET CRAIG'

| Characteristic | New Cultivar 'HARVEST MOON' | Comparison Cultivar 'JANET CRAIG' (unpatented) |
|---|---|---|
| Growth Habit | More upright | Less upright |
| Leaf Color | Bright yellow with thin green stripes | All green |
| Leaf Length | About 50% longer than 'JANET CRAIG' | |
| Leaf Texture | Smooth | Slightly ribbed |

BRIEF DESCRIPTION OF THE PHOTOGRAPHS

The accompanying photographs illustrate the overall appearance of the new *Dracaena* cultivar 'HARVEST MOON' showing the colors as true as is reasonably possible with colored reproductions of this type. Colors in the photographs may differ slightly from the color value cited in the detailed botanical description which accurately describe the color of 'HARVEST MOON'.

Figure 2:
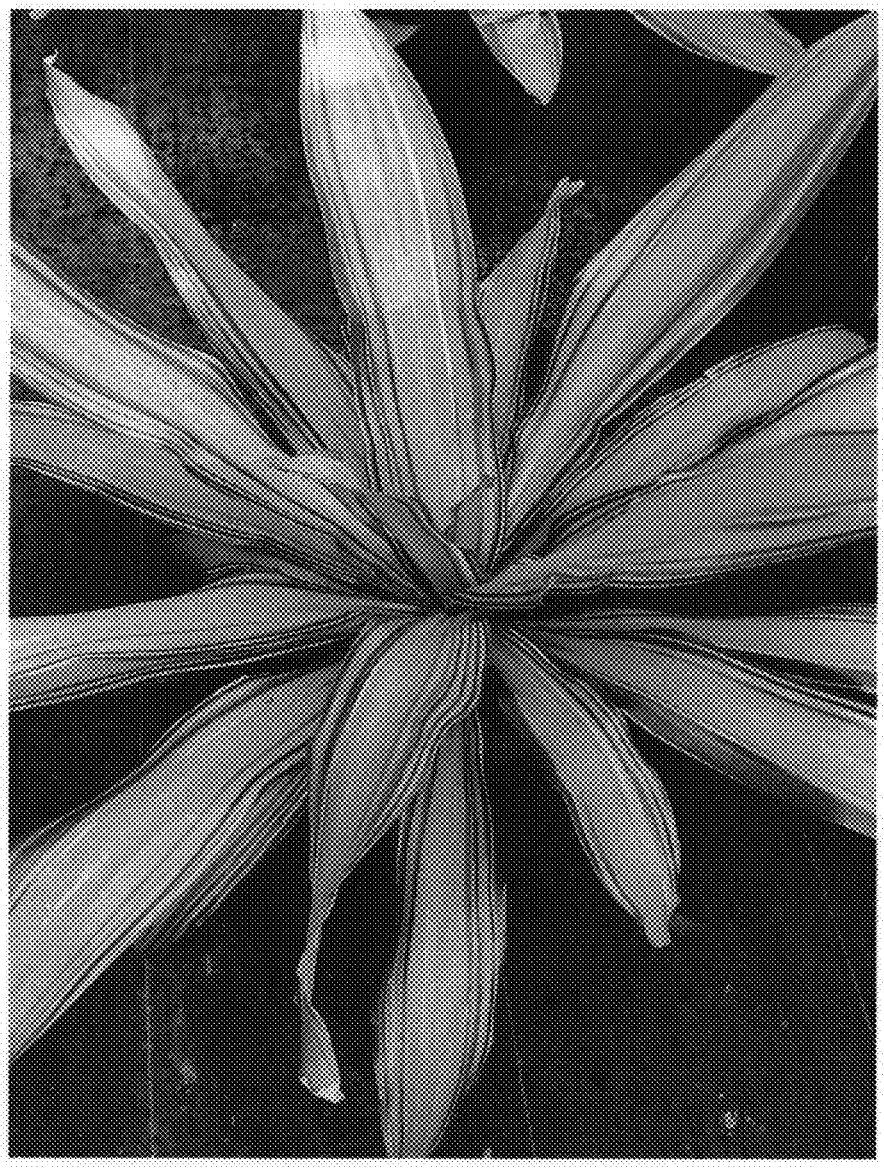

FIG. 1—shows a top-down view of a typical plant of 'HARVEST MOON' at 6 months of age;

FIG. 2—shows a side view a typical plant of 'HARVEST MOON' at 6 months of age;

DETAILED BOTANICAL DESCRIPTION

The new *Dracaena* 'HARVEST MOON' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe the new *Dracaena* cultivar 'HARVEST MOON' as grown in a shade house with 60% shade level in Homestead, Fla., USA, under conditions which closely approximate those generally used in commercial practice. The average daytime temperature ranges from 24-30° C. and fertilization is with Nutricote 18-6-8 T180. Color references are made to The Royal Horticultural Society Colour Chart (R.H.S.), except where general colors of ordinary significance are used. The photographs and descriptions were taken during the Spring season in Homestead, Fla., USA. The age of the plants described is 6 months after cutting.

Classification:

*Botanical.*—*Dracaena deremensis.*

*Variety name.*—HARVEST MOON.

Parentage: Naturally-occurring mutation of *Dracaena deremensis* 'NOTCANE' (unpatented).

Optimal growth conditions:

*Light intensities.*—Partial sunlight.

*Temperature.*—Day: 24° C. to 30° C. Night: 20° C. to 24° C.

*Temperature tolerance.*—Tolerant to a low temperature of about 4° C. and tolerant to a high temperature of about 36° C.

*Fertilization.*—A balanced fertilizer with level of 200 ppm Nitrogen.

*Growth regulators.*—None.

Propagation:

*Type.*—Vegetative cuttings.

*Time to initiate roots.*—About 7 to 10 days at 28° C.

*Time to produce a rooted cutting.*—About 14 to 21 days at 28° C.

Plant:

General appearance and form:

*Height.*—About 70 cm when grown in ground; about 75 cm when grown in a 25 cm size container.

*Spread.*—About 90 cm when grown in ground; About 90 cm when grown in 25 cm size container.

*Form.*—Dicot; leaves whorled, leaf bases wrap around the stem.

*Shape.*—Linear.

*Growth rate and habit.*—About 60 cm per year, upright.

*Fragrance.*—None.

*Stem.*—Length: About 50 cm when grown in ground; About 60 cm when grown in 25 cm size container. Diameter: About 4 cm to 5 cm Shape: Round Color: RHS 149A Texture: Smooth. Strength: Stiff. Internode length: About 5 mm to 8 mm.

Foliage:

*Quantity.*—About 20-30 leaves per plant.

*Arrangement and attachment.*—Single, alternate; leaves whorled; leaf bases wrap around the stem.

*Leaf length.*—About 65 cm.

*Leaf width.*—About 9 cm.

*Overall shape of leaf.*—Linear.

*Apex shape.*—Acute.

*Base shape.*—Attenuate.

*Margin.*—Entire.

*Texture.*—Upper Surface: Smooth, slightly waxy Under Surface: Smooth.

*Pubescence, upper and lower surfaces.*—None.

*Color of mature leaf.*—Upper Surface: Yellow-green RHS 149A, with pale cream RHS 3D stripes Lower Surface: Yellow-green RHS 149A, with pale cream RHS 3D stripes.

*Color of immature leaf.*—Upper Surface: Yellow-green RHS 149A, with pale cream RHS 3D stripes Lower Surface: Yellow-green RHS 149A, with pale cream RHS 3D stripes.

*Venation.*—Pattern: Parallel Color: Upper surface: Dark Green RHS 141A Lower surface: Dark Green RHS 141A.

*Leaf fragrance.*—None.

*Leaf sheath.*—Length:4 cm Width: 4 cm Texture: Stiff Color: Pale Cream RHS 3D.

Inflorescence description: No flowering observed.

Reproductive organs: No reproductive organs observed.

Disease/pest resistance: Somewhat resistant to mealybugs (few observed).

Disease/pest susceptibility: Low.

We claim:

1. A new and distinct *Dracaena deremensis* plant named 'HARVEST MOON', substantially as illustrated and described herein.

* * * * *